United States Patent [19]
Floc'h et al.

[11] Patent Number: 5,827,822
[45] Date of Patent: Oct. 27, 1998

[54] CYCLOSPORIN A FORMULATIONS AS NANOPARTICLES

[75] Inventors: Robert Floc'h, Nantes; Christian Merle, Poitiers, both of France

[73] Assignee: Sangstat Medical Corporation, Menlo Park, Calif.

[21] Appl. No.: 622,516

[22] Filed: Mar. 25, 1996

[51] Int. Cl.$^6$ .............................. A61K 9/10; A61K 38/13
[52] U.S. Cl. .............................................. 514/11; 514/938
[58] Field of Search .................................. 530/317, 321; 514/9, 11, 938; 424/450

[56] References Cited

U.S. PATENT DOCUMENTS

| | | | |
|---|---|---|---|
| 4,117,118 | 9/1978 | Harri et al. | 514/11 |
| 4,220,641 | 9/1980 | Traber et al. | 514/11 |
| 4,388,307 | 6/1983 | Cavanak | 514/11 |
| 4,792,449 | 12/1988 | Ausman et al. | 424/440 |
| 4,889,723 | 12/1989 | Kim et al. | 424/450 |
| 4,970,076 | 11/1990 | Horrobin | 424/456 |
| 4,990,337 | 2/1991 | Kurihara et al. | 424/427 |
| 4,996,193 | 2/1991 | Hewitt et al. | 514/11 |
| 5,047,396 | 9/1991 | Orban et al. | 514/11 |
| 5,051,402 | 9/1991 | Kurihara et al. | 514/11 |
| 5,118,493 | 6/1992 | Kelley et al. | 514/11 |
| 5,154,930 | 10/1992 | Popescu et al. | 424/450 |
| 5,206,219 | 4/1993 | Desai | 514/3 |
| 5,342,625 | 8/1994 | Hauer et al. | 424/455 |
| 5,350,741 | 9/1994 | Takada | 514/3 |
| 5,364,632 | 11/1994 | Benita et al. | 424/450 |
| 5,389,382 | 2/1995 | List et al. | 424/499 |
| 5,474,979 | 12/1995 | Ding et al. | 514/11 |
| 5,504,068 | 4/1996 | Komiya et al. | 514/11 |
| 5,540,931 | 7/1996 | Hewitt et al. | 424/434 |
| 5,583,105 | 12/1996 | Kovacs et al. | 514/11 |
| 5,614,491 | 3/1997 | Walch et al. | 514/11 |

FOREIGN PATENT DOCUMENTS

| | | |
|---|---|---|
| 2009533 | 8/1990 | Canada . |
| 1326995 | 2/1994 | Canada . |
| 2106827 | 3/1994 | Canada . |
| 2137025 | 11/1994 | Canada . |
| 572942 | 12/1993 | European Pat. Off. . |
| 0 589 843 | 3/1994 | European Pat. Off. . |
| 650721 | 5/1995 | European Pat. Off. . |
| 2015339 | 9/1979 | United Kingdom . |
| 2200048 | 7/1988 | United Kingdom . |
| 2209671 | 5/1989 | United Kingdom . |
| 2221157 | 1/1990 | United Kingdom . |
| 2224205 | 5/1990 | United Kingdom . |
| 2228198 | 8/1990 | United Kingdom . |
| 91/16057 | 10/1991 | WIPO . |
| 92/09299 | 6/1992 | WIPO . |
| 92/18105 | 10/1992 | WIPO . |
| 93/01106 | 1/1993 | WIPO . |
| 93/23010 | 11/1993 | WIPO . |
| 94/23733 | 10/1994 | WIPO . |
| 95/06464 | 3/1995 | WIPO . |

OTHER PUBLICATIONS

Tarr et al. "Enhanced Intestinal Absorption of Cyclosporine in Rats Through the Reduction of Emulsion Droplet Size." Pharm. Res. vol. 6, pp. 40–43, 1989.

Abdallah et al. "The Preparation and Evaluation of a Tablet Dosage Form of Cyclosporine in Dogs." Pharm. Res. vol. 8, pp. 518–522, 1991.

Sato et al. "Enhancement of The Intestinal Absorption of Cyclosporine Derivative by Milk Fat Globule Membrane." Biol. Pharm. Bull. vol. 17, pp. 1526–1528, 1994.

Benmoussa et al. "Cyclosporin Absorption Is Impaired by the Fat Substitutes, Sucrose Polyester and Tricarballylate Triester, in the Rat." Pharm. Res. vol. 11, pp. 1458–1461, 1994.

Trull et al. "Cyclosporin Absorption From Microemulsion Formulation in Liver Transplant Recipient." The Lancet. vol. 341, p. 433, 1993.

Ferrea et al. "Oral Microemulsion Formulation Substitutes for Intravenous Cyclosporin in Child with Graft–Versus–Host Disease." The Lancet. vol. 344, pp. 480–481, 1994.

Reymond et al. "In Vivo Model for Ciclosporin Intestinal Absorption in Lipid Vehicles." Pharm. Res. vol. 5, pp. 677–679, 1988.

Ritschel et al. "Improvement of Peroral Absorption of Cyclosporine A By Microemulsions." Meth. Find Exp. Clin. Pharmacol. vol. 12, pp. 127–134, 1990.

Reymond et al. "In Vitro Model for Ciclosporin Intestinal Absorption in Lipid Vehicles." Pharm. Res. vol. 5, pp. 673–676, 1988.

Cavanak et al. "Formulation of Dosage Forms." Prog. Allergy. vol. 38, pp. 65–72, 1986.

*Primary Examiner*—Jeffrey E. Russel
*Attorney, Agent, or Firm*—Richard F. Trecartin; Mark T. Kresnak; Flehr, Hohbach, Test, Albritton and Herbert

[57] ABSTRACT

Cyclosporin A formulations are provided as amorphous nanoparticle dispersions for physiologic absorption. The compositions have high bioavailability and patient acceptability. By providing for concentrates comprising lower alkanols and a polyoxyalkylene surfactant as a stable dispersion of cyclosporin A, upon introducing the stable dispersion into an aqueous medium, the subject formulation is produced comprising amorphous bioavailable cyclosporin nanoparticles.

13 Claims, No Drawings

CYCLOSPORIN A FORMULATIONS AS NANOPARTICLES

BACKGROUND OF THE INVENTION

The drug cyclosporin A, despite its many shortcomings and the difficulties in formulation, variations in bioavailability, and side effects, has proven to be one of the great success stories of the drug industry. Because of cyclosporin A's hydrophobicity, formulations of cyclosporin A must take into account the need for a stable dispersion of the cyclosporin A, as well as the manner of administration of the formulation. For example, if it is intended that the formulation be diluted with water prior to its being taken orally, the resulting composition must provide the cyclosporin A in a bioavailable form, where adverse effects are not enhanced, preferably diminished. The cyclosporin A which will come out of solution should be dispersable, so that the dosage is repeatable. Alternatively, where the formulation is provided in a manner where the cyclosporin A formulation becomes diluted with gastric juices, such as the use of capsules, it is essential that the cyclosporin A retains its bioavailability and activity in the environment of the gastric juices. In all events, the cyclosporin A must be able to be transported into the vascular system, where it can diminish the immune response.

It is therefore of interest to develop formulations which are organoleptically acceptable, provide for desirable levels of bioavailability, do not introduce adverse effects associated with cyclosporin A, and generally fulfill the requirements of therapeutic formulations.

BRIEF SUMMARY OF THE INVENTION

Aqueous dispersions of cyclosporin are provided by introducing a stable dispersion of cyclosporin in a formulation comprising as co-solvents a lower alkanol and a polyoxyalkylene surfactant, and desirably a polyethylene glycol, as co-solvent. Upon dilution of the stable dispersion, an aqueous dispersion is obtained comprising nanoparticles of cyclosporin in amorphous form having good bioavailability.

DETAILED DESCRIPTION

Methods and compositions are provided for producing an aqueous colloidal dispersion of cyclosporin nanoparticles having good bioavailability. The nanoparticles are substantially spheric, the cyclosporin is present in an amorphous form, and the average size will generally be less than about 1000 nm, greater than about 50 nm, generally in the range of about 200–800 nm, usually in the range of about 200–600 nm. Generally, at least about 50 weight percent of the total weight of cyclosporin will be present as particles in the indicated size range. Larger particles may be present, particularly as aggregates of nanoparticles, where the average diameter will usually be less than about 50 μm, more usually less than about 25 μm, the aggregates usually not exceeding 40 weight % of the total cyclosporin.

The amount of cyclosporin A amorphous particles in the composition will be sufficient for therapeutic effect. Since the formulation may be formed by introduction into an aqueous medium prior to administration or directly into the gastric juices, the particular concentration cannot be stated, since the dilution in the stomach is uncertain. For preparation in an aqueous medium prior to oral administration, generally, the cyclosporin will be present at a weight percent of about 0.01–2.5, more usually from about 0.01–0.5 weight percent. The temperature of mixing may be in the range of about 10° to 50° C., usually in the range of about 20° to 40° C. Usually the mixing will involve stirring for sufficient time to provide the solution of the cyclosporin.

The colloidal amorphous suspension of the nanoparticles is sufficiently stable to allow for some standing prior to administration, frequently up to about 6 hours, more frequently up to about 3 hours.

While cyclosporin A finds primary use, any of the cyclosporins which are physiologically acceptable, e.g. A through Z, may be employed.

The amorphous cyclosporin colloidal dispersion may be produced by preparing a stable dispersion of cyclosporin in a lower alkanol and a polyoxyalkylene compound, either ester or alcohol. The alkanols will be ethanol or propylene glycol, individually or in combination, particularly where ethanol will be present in the range of about 25–75 volume percent, when the combination of alkanols is employed. The particular manner in which the colloidal dispersion is produced is not critical, so long as the materials used in the stable dispersion are physiologically acceptable, do not interfere with the activity of the cyclosporin, and are readily available.

Various polyalkyleneoxy compounds may be employed which may serve as surfactants and co-solvents with the lower alkanols. The polyalkyleneoxy compounds are, therefore, liquids, soluble in both water and lower alkanols, have low toxicity and in conjunction with the lower alkanols are capable of maintaining a stable dispersion, usually a solution of cyclosporin A. Exemplary of polyoxyethylene surfactants are polyoxyethylene esters, such as polyoxyethylene substituted sorbitan esterified with a fatty acid of from 12–18 carbon atoms, more usually from about 16–18 carbon atoms, exemplified by polysorbate 80. The number of oxyethylene groups will generally be from about from 10–30. Exemplary of polyoxyalkylene compounds as cosolvents are polyethylene glycols of an average molecular weight of less than about 2000, preferably less than about 1000, at least about 300, more usually in the range of about 300–700 particularly from about 350–500 kiloDaltons. Generally, greater than 50% by weight of the polyethylene glycol will be within 50% of the average molecular weight of the polyethylene glycol.

In the formulation, the total amount of lower alkanol will generally be in the range of about 25–60 weight percent, more usually in the range of about 30–50 weight percent. The total amount of alkyleneoxy compound(s) will generally be in the range of about 20–50 weight percent, more usually in the range of about 25–40 weight percent. Where combinations of polyoxyalkylene compounds are employed, the amount of the fatty acid ester will generally range from about 25–100% of the polyoxyalkylene compounds.

The weight of cyclosporin in the formulation will be sufficient to provide for a therapeutic dosage, generally in the range of about 2.5 to 25 weight percent, more usually in the range of about 5–15 weight percent.

The subject compositions may be prepared by first dissolving the cyclosporin in the lower alkanol, where a small proportion of the polyoxyalkylene compound may also be included, generally less than about 50 weight percent of the composition used for dissolving the cyclosporin. An elevated temperature may be employed, usually in the range of about 60° to 90° C. After dissolving the cyclosporin, the major proportion of the polyalkyleneoxy compound may be added and the total formulation brought to the desired ratios by the addition of the appropriate components. Generally, the cyclosporin can be dissolved in the lower alkanol (optionally including a portion of the polyalkyleneoxy compound) at a weight ratio of about 1:1.5–5, more usually 1:2–4.

The subject formulations may be used in accordance with conventional ways already described in the literature. Oral formulations have been reported in U.S. Pat. Nos. 4,388,307; and 5,342,625; and UK Patent No. 2,222,770B, whose disclosures are incorporated herein by reference as describing the use of cyclosporin in oral formulations. Thus, the subject compositions may be administered as liquid solutions, capsules, or the like, taken orally in single or multiple dosages, as therapeutically required in accordance with conventional procedures. The formulations are used with patients who require that they be immunocompromised, as in the case of transplantation, autoimmune diseases and the like.

For convenience of the user, kits may be provided having the appropriate amount of cyclosporin, one or more dosage levels and the cosolvents, namely the lower alkanol(s) and the polyalkyleneoxy compound(s), e.g. at least one of ethanol and propylene glycol and at least one of polysorbate 80 and PEG400.

The following examples are offered by way of illustration and not by way of limitation.

EXAMPLE 1

5 g of cyclosporin A was added to 5 mL of ethanol. The mixture was stirred to complete dissolution of cyclosporin A. To the resulting solution were added 25 g of polysorbate 80 and the volume is completed to 50 mL by 1,2-propylene glycol. The mixture was sufficiently stirred at room temperature until a homogeneous solution was formed.

EXAMPLE 2

5 g of cyclosporin A was added to 5 mL of ethanol. The mixture was stirred until complete dissolution of cyclosporin A. To the resulting solution were added 15 g of polysorbate 80 and the volume is completed to 50 mL by a mixture of 1,2-propylene glycol and polyethylene glycol 400. The mixture was sufficiently stirred at room temperature until a homogeneous solution was formed.

EXAMPLE 3

1 mL of the solution obtained in example 1 was added in 50 mL of water with a glass syringe as recommended for the oral administration of concentrated emulsions or microemulsions in human. The addition of the solution was followed by a quick dissolution and a white suspension of fine particles was obtained having a blue reflect as colloidal suspensions (Tyndall effect). After centrifugation at 26,000 g during 5 hours, the sediment was washed with water and then centrifuged at 26,000 g during 24 hours. The washing and centrifugation processes were repeated twice under the same conditions. After drying, an x-ray powder diagram was performed. The solid was exclusively in amorphous form.

The sediment was examined by scanning electron microscopy. The sediment was constituted of amorphous spheric nanoparticles with a diameter between 200 and 400 nm with the presence of some aggregates.

2 mL of the solution obtained in example 1 was added in 100 mL of water and the colloidal suspension was examined 10 minutes and 1 hour after the dilution by a diffraction/diffusion laser granulometer (Malvern SB.OD).

After 1 hour, two particle populations were observed: one representing 70% of the weight of cyclosporin A with an average diameter of 300 nm and a second one representing 30% of the weight of cyclosporin A with an average diameter of 20 $\mu$m, probably constituting aggregates of nanoparticles.

EXAMPLE 4

1 mL of the solution obtained in example 1 was added to 50 mL of water and the colloidal suspension was stirred during 10 minutes.

The suspension was then added to 200 mL of artificial acidic gastric juice and warmed at 37° C. The homogeneous colloidal suspension was examined by diffraction/diffusion laser granulometry (Malvern SB.OD). The suspension was constituted exclusively of nanoparticles with an average diameter of 600 nm.

EXAMPLE 5

1 mL of the solution obtained in example 1 was added directly to 200 mL of artificial acidic gastric juice.

The homogeneous suspension was warmed at 37° C. and examined rapidly by diffraction/diffusion laser granulometry (Malvern SB.OD). The suspension was exclusively constituted of nanoparticles with an average diameter of 350 nm.

The subject cyclosporin compositions provide for excellent bioavailability in being amorphous particles, small, so as to have high surface area, and without detrimental effects other than those conventionally found with cyclosporin.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An aqueous suspension of cyclosporin nanoparticles, wherein at least 50 weight percent of the cyclosporin present in the suspension is of particles less than about 1 $\mu$m, said cyclosporin nanoparticles being amorphous and wherein said suspension comprises at least one of a polyoxyethylene surfactant or a polyethylene glycol of less than about 2000 Daltons.

2. A suspension according to claim 1, comprising in minor amounts lower alkanol and at least one polyoxyethylene surfactant.

3. A suspension according to claim 2, wherein said polyoxyethylene surfactant is polysorbate 80.

4. A suspension according to claim 2, wherein said lower alkanol is at least one of ethanol and propylene glycol.

5. A suspension according to claim 1, comprising a polyethylene glycol of less than about 2000 Daltons.

6. In a method for orally administering cyclosporin to a patient, the improvement which comprises:
   providing said cyclosporin as an aqueous suspension, wherein at least 50 weight % of said cyclosporin in said suspension is as amorphous nanoparticles of less than about 1000 nm, and
   orally administering said cyclosporin suspension to said patient.

7. A method according to claim 6, wherein said providing comprises adding to an aqueous medium a composition comprising cyclosporin suspended in a combination of lower alkanol consisting of at least one of ethanol and propylene glycol and a polyoxyethylene surfactant.

8. A method for preparing an aqueous suspension of cyclosporin nanoparticles according to claim 1 comprising:

combining at least one of ethanol and propylene glycol with cyclosporin A to form a solution;

combining said solution with a polyethyleneoxy surfactant to form a second solution, and diluting said second solution with water to form an aqueous suspension of amorphous nanoparticles of said cyclosporin A.

9. In a method for orally administering cyclosporin to a patient, the improvement which comprises:

providing a cyclosporin suspension, wherein at least 50 weight % of said cyclosporin in said suspension is as amorphous nanoparticles of less than about 1000 nm and wherein said cyclosporin suspension is prepared by a method comprising adding to an aqueous medium a composition comprising cyclosporin, a lower alkanol consisting of at least one of ethanol and propylene glycol and polysorbate 80, and orally administering said cyclosporin suspension to said patient.

10. In a method for orally administering cyclosporin to a patient, the improvement which comprises:

providing a cyclosporin suspension, wherein at least 50 weight % of said cyclosporin in said suspension is as amorphous nanoparticles of less than about 1000 nm and wherein said cyclosporin suspension is prepared by a method comprising adding to an aqueous medium a composition comprising cyclosporin, a lower alkanol consisting of at least one of ethanol and propylene glycol and a polyoxyethylene surfactant, and wherein said lower alkanol is present in from about 25 to 60 weight percent, said polyoxyalkylene surfactant is present in from about 20 to 50 weight percent, and said cyclosporin is present in from about 2.5 to 25 weight percent, and orally administering said cyclosporin suspension to said patient.

11. In a method for orally administering cyclosporin to a patient, the improvement which comprises:

providing a cyclosporin suspension, wherein at least 50 weight % of said cyclosporin in said suspension is as amorphous nanoparticles of less than about 1000 nm and wherein said cyclosporin suspension is prepared by a method comprising adding to an aqueous medium a composition comprising cyclosporin, a lower alkanol consisting of at least one of ethanol and propylene glycol, a polyoxyethylene surfactant and a polyoxyethylene cosolvent of less than 2000 Daltons, and orally administering said cyclosporin suspension to said patient.

12. An aqueous suspension of cyclosporin nanoparticles, wherein at least 50 weight percent of the cyclosporin present in the suspension is of particles less than about 1 $\mu$m, wherein said cyclosporin nanoparticles are amorphous and have a density greater than that of the aqueous solution in which they are suspended and wherein said suspension comprises at least one of a polyoxyethylene surfactant or a polyethylene glycol of less than about 2000 Daltons.

13. An aqueous suspension of nanoparticles that consists essentially of cyclosporin and at least one of a polyoxyethylene surfactant or a polyethylene glycol of less than about 2000 Daltons, wherein at least 50 weight percent of the cyclosporin present in the suspension is of particles less than about 1 $\mu$m and wherein said cyclosporin nanoparticles are amorphous.

* * * * *